(12) United States Patent
Matsumura et al.

(10) Patent No.: US 11,172,870 B2
(45) Date of Patent: Nov. 16, 2021

(54) DEMENTIA SYMPTOM DETECTION SYSTEM AND PROGRAM

(71) Applicant: Panasonic Intellectual Property Management Co., Ltd., Osaka (JP)

(72) Inventors: Yoshihiro Matsumura, Osaka (JP); Takashi Nishiyama, Hyogo (JP); Mikio Iwakawa, Osaka (JP); Kengo Abe, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 636 days.

(21) Appl. No.: 16/067,612

(22) PCT Filed: Jan. 16, 2017

(86) PCT No.: PCT/JP2017/001163
§ 371 (c)(1),
(2) Date: Jul. 1, 2018

(87) PCT Pub. No.: WO2017/145566
PCT Pub. Date: Aug. 31, 2017

(65) Prior Publication Data
US 2019/0015036 A1    Jan. 17, 2019

(30) Foreign Application Priority Data

Feb. 22, 2016   (JP) .............................. JP2016-031522

(51) Int. Cl.
| | |
|---|---|
| *A61B 5/00* | (2006.01) |
| *G08B 21/04* | (2006.01) |
| *G16H 50/20* | (2018.01) |
| *G08B 25/04* | (2006.01) |
| *G16H 50/30* | (2018.01) |
| *G16H 80/00* | (2018.01) |
| *A61B 5/16* | (2006.01) |

(Continued)

(52) U.S. Cl.
CPC ............ *A61B 5/4088* (2013.01); *A61B 5/002* (2013.01); *A61B 5/0077* (2013.01); *A61B 5/165* (2013.01);
(Continued)

(58) Field of Classification Search
CPC ... A61B 5/4088; A61B 5/1118; A61B 5/0022; A61B 5/165; G16H 50/30; G09B 19/00
See application file for complete search history.

(56) References Cited

U.S. PATENT DOCUMENTS

| | | |
|---|---|---|
| 2002/0091326 A1 | 7/2002 | Hashimoto et al. |
| 2004/0098144 A1 | 5/2004 | Hashimoto et al. |

(Continued)

FOREIGN PATENT DOCUMENTS

| | | |
|---|---|---|
| JP | 2002-119485 | 4/2002 |
| JP | 2003-153868 | 5/2003 |

(Continued)

OTHER PUBLICATIONS

International Search Report (ISR) dated Mar. 7, 2017 in International (PCT) Application No. PCT/JP2017/001163.
(Continued)

*Primary Examiner* — Jerry-Daryl Fletcher
(74) *Attorney, Agent, or Firm* — Renner, Otto, Boisselle & Sklar, LLP

(57) ABSTRACT

A dementia symptom detection system includes an information processor which determines the level of dementia of a user based on (i) a reference value which is for an index corresponding to behavioral and psychological symptoms of dementia and which is determined based on the history of the activity amount stored in storage and the history of device operation information stored in the storage, and (ii) a personal value of the user which is for the index and which is determined based on the detected activity amount of the user and the obtained device operation information of the user.

12 Claims, 11 Drawing Sheets

(51) Int. Cl.
   *A61B 5/22*   (2006.01)
   *A61B 5/11*   (2006.01)
   *G16H 20/70*  (2018.01)
(52) U.S. Cl.
   CPC .......... *A61B 5/6889* (2013.01); *A61B 5/7257* (2013.01); *A61B 5/7275* (2013.01); *G08B 21/0407* (2013.01); *G08B 21/0484* (2013.01); *G08B 21/0492* (2013.01); *G08B 25/04* (2013.01); *G16H 50/20* (2018.01); *G16H 50/30* (2018.01); *G16H 80/00* (2018.01); *A61B 5/0022* (2013.01); *A61B 5/1118* (2013.01); *A61B 5/167* (2013.01); *A61B 5/22* (2013.01); *A61B 5/4815* (2013.01); *A61B 5/6887* (2013.01); *A61B 2560/0209* (2013.01); *A61B 2562/0219* (2013.01); *G16H 20/70* (2018.01)

(56) References Cited

U.S. PATENT DOCUMENTS

2006/0094938 A1    5/2006   Shimada
2009/0256710 A1   10/2009   Duckert
2013/0095459 A1*   4/2013   Tran ..................... A61B 5/021
                                                       434/247
2014/0194756 A1    7/2014   Sazuka
2017/0095193 A1*   4/2017   Shin ..................... G16H 10/60
2018/0125409 A1*   5/2018   Tahara .................. H04N 13/10

FOREIGN PATENT DOCUMENTS

| JP | 2004-295861 | 10/2004 |
| JP | 2006-72443  | 3/2006  |
| JP | 2006-129887 | 5/2006  |
| JP | 2007-190306 | 8/2007  |
| JP | 2007-282992 | 11/2007 |
| JP | 2009-254817 | 11/2009 |
| JP | 2010-178920 | 8/2010  |
| JP | 2010-207537 | 9/2010  |
| JP | 2011-072644 | 4/2011  |
| JP | 2012-239799 | 12/2012 |

OTHER PUBLICATIONS

Office Action issued by the Japanese Patent Office for corresponding Japanese patent application No. 2018-501039 dated Oct. 15, 2019.

* cited by examiner

FIG. 2

| SYMPTOMS | | DETECTION METHOD |
|---|---|---|
| BEHAVIORAL SYMPTOMS | WANDERING | NIGHT-TIME ACTIVITY AMOUNT |
| | SLEEP DISTURBANCE | ACTIVITY AMOUNT DURING SLEEP |
| | EATING DISORDER | DEVICE OPERATION INFORMATION OF REFRIGERATOR, POT, MICROWAVE, ETC. |

FIG. 3

| SYMPTOMS | | DETECTION METHOD |
|---|---|---|
| PSYCHOLOGICAL SYMPTOMS | DEPRESSION | DAYTIME ACTIVITY AMOUNT (REDUCTION IN ACTIVITY AMOUNT) |
| | ANXIETY | DEVICE OPERATION INFORMATION OF TV OR INFORMATION DEVICE (ABNORMAL USE) |
| | MISIDENTIFICATION | DEVICE OPERATION INFORMATION OF ELECTRICAL HOUSEHOLD APPLIANCE (ABNORMAL USE) |

DEMENTIA SYMPTOM DETECTION SYSTEM AND PROGRAM

TECHNICAL FIELD

The present invention relates to a dementia symptom detection system and a program.

BACKGROUND ART

Core symptoms such as memory impairment, disorientation, reduced comprehension and judgment, and reduced executive function are known as symptoms of dementia. Having such core symptoms, a dementia patient has behavioral and psychological symptoms of dementia (BPSD) depending on, for example, the patient's personality, and the influence of the surrounding environment.

As a technique for detecting the disorders of residents due to dementia or the like, Patent Literatures (PTLs) 1 and 2 disclose a lifestyle disorder detection method for detecting unusual behavior of the residents.

CITATION LIST

Patent Literature

PTL 1: Japanese Unexamined Patent Application Publication No. 2006-72443
PTL 2: Japanese Unexamined Patent Application Publication No. 2004-295861

SUMMARY OF THE INVENTION

Technical Problem

Although the above described technique detects the unusual behavior of the residents, it is insufficient to detect the signs of dementia.

The present invention provides a dementia symptom detection system and a program capable of appropriately detecting the signs of dementia.

Solution to Problem

A dementia symptom detection system according to one aspect of the present invention includes a detector which detects an activity amount of a user; an obtainment unit which obtains device operation information of the user; a storage which stores a history of the activity amount and a history of the device operation information; an information processor which determines a level of dementia of the user based on (i) a reference value for an index corresponding to behavioral and psychological symptoms of dementia, and (ii) a personal value of the user for the index, the reference value being determined based on at least one of the history of the activity amount stored in the storage and the history of the device operation information stored in the storage, the personal value being determined based on at least one of the activity amount of the user detected and the device operation information of the user obtained; and a presentation unit which presents the level of dementia of the user determined by the information processor.

A program according to one aspect of the present invention is a program for causing a computer to function as the dementia symptom detection system.

Advantageous Effect of Invention

According to the present invention, it is possible to appropriately detect the signs of dementia.

BRIEF DESCRIPTION OF DRAWINGS

FIG. 2 illustrates information for detecting the signs of behavioral symptoms.
FIG. 3 illustrates information for detecting the signs of psychological symptoms.

DESCRIPTION OF EXEMPLARY EMBODIMENT

Figure 1:
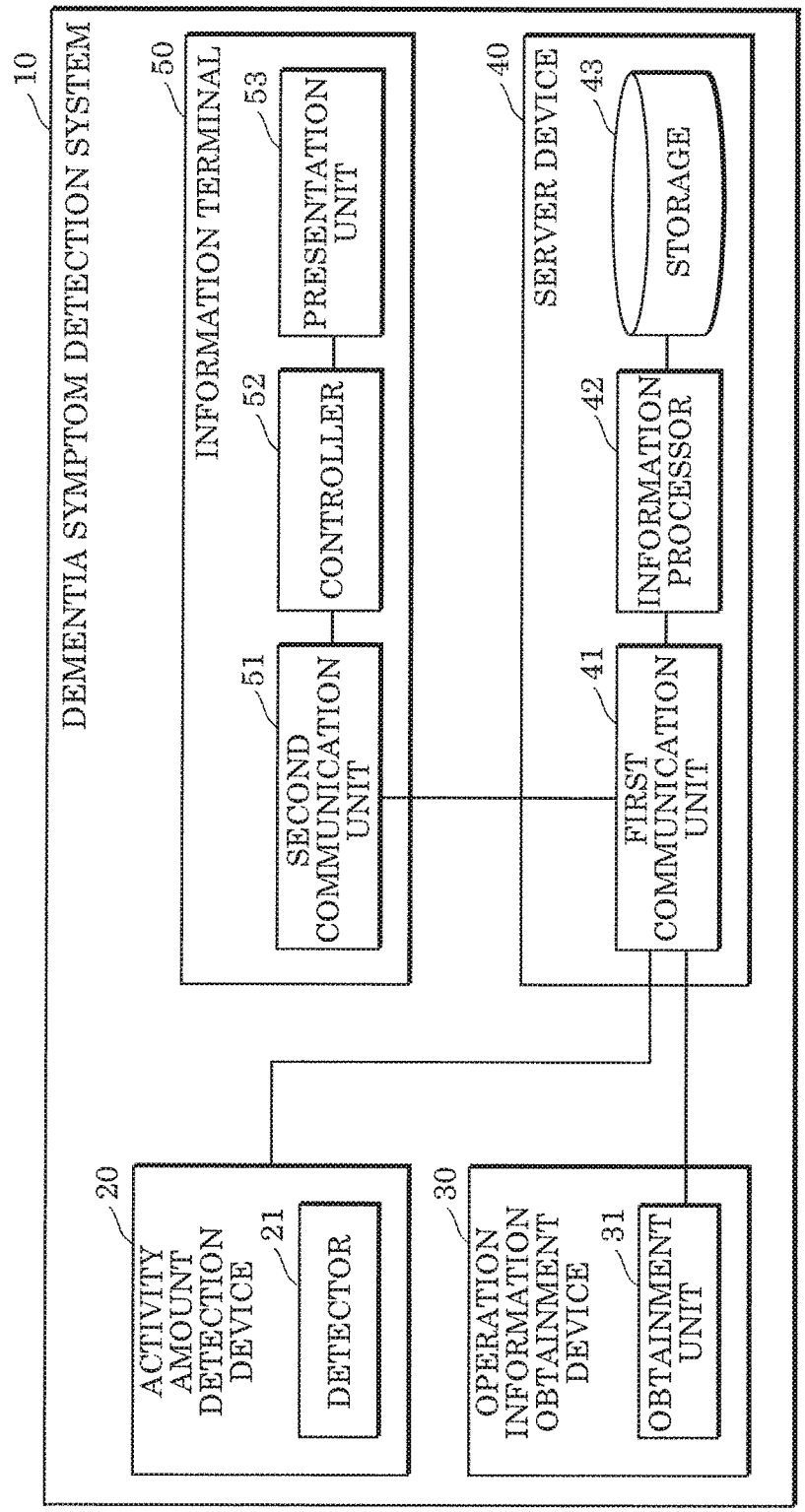
FIG. 1 is a block diagram illustrating a configuration of a dementia symptom detection system according to an embodiment.

Hereinafter, an embodiment will be described with reference to the drawings. Note that the embodiment described below shows a general or specific example. The numerical values, shapes, materials, structural elements, the arrangement and connection of the structural elements, steps, the order of the steps, etc., indicated in the following embodiment are mere examples, and therefore do not intend to limit the inventive concept. Among the structural elements in the following embodiment, those not recited in any of the independent claims defining the most generic part are described as optional structural elements.

Note that the drawings are represented schematically and are not necessarily precise illustrations. Moreover, like reference signs indicate like structural elements in the drawings, and overlapping descriptions thereof may be omitted or simplified.

EMBODIMENT

Configuration of Dementia Symptom Detection System

First, a description will be given of an overall configuration of a dementia symptom detection system according to an embodiment. FIG. 1 is a block diagram illustrating a configuration of the dementia symptom detection system according to the embodiment.

Dementia symptom detection system 10 is a system which is capable of catching changes in behavioral and psychological symptoms specific to dementia, and informing the subject of detection (hereinafter, also referred to as a user) or the family of the subject of the signs of dementia. Specifically, dementia symptom detection system 10 identifies a personal value for an index corresponding to BPSD of the user, and compares the identified personal value with the reference value for the index to detect the signs of dementia. The reference value for the index is identified (calculated) based on the history of the activity amount and the history of device operation information.

In this way, the index corresponding to the BPSD is used for determining the level of dementia, which allows dementia symptom detection system 10 to appropriately detect the signs of dementia. Moreover, dementia symptom detection system 10 is capable of presenting the presence of the signs of dementia, which allows early recognition of the dementia symptoms.

Note that the history of the activity amount and the history of the device operation information may be about the user (the subject of detection), or about another user who is normal and different from the user (the subject of detection) and who is considered to have no signs of dementia.

As illustrated in FIG. 1, dementia symptom detection system 10 includes activity amount detection device 20, operation information obtainment device 30, server device 40, and information terminal 50.

Activity amount detection device 20 is a device provided in the user's residence (living space). Activity amount detection device 20 may be a device worn by the user. Activity amount detection device 20 includes detector 21 which detects the activity amount of the user. Specific examples of detector 21 include a pyroelectric sensor (infrared sensor), a Doppler sensor, a radio wave sensor, and a wearable activity meter (acceleration sensor). Moreover, detector 21 may be a mat type or radio wave type sleep sensor which detects the activity amount of the user during sleep. Moreover, activity amount detection device 20 does not have to be a detection-specific device. For example, activity amount detection device 20 may be an electrical household appliance such as an air conditioner, and detector 21 may be a sensor included in such an electrical household appliance.

Activity amount detection device 20, for example, calculates the number of times the sensor is turned on and off per unit time as the activity amount of the user in the unit time, and transmits the calculated result to server device 40. The time information (time stamp) indicating the time of the detection of the activity amount is desirably added to the activity amount. Note that when detector 21 is, for example, a Doppler sensor or a radio wave sensor, the strength or the like of the motion may be calculated.

Although not illustrated in FIG. 1, more specifically, activity amount detection device 20 includes a calculator which calculates the activity amount, a timer (a timer circuit) for adding the time information to the activity amount, and a communication unit which transmits the calculated activity amount to server device 40. Note that the calculator is not an essential structural element. It may be that activity amount detection device 20 transmits the detection result (raw data) of detector 21 to server device 40, and that server device 40 calculates the activity amount based on the received detection result.

Operation information obtainment device 30 is a device provided in the user's residence. Operation information obtainment device 30 may be a device carried by the user. Operation information obtainment device 30 includes obtainment unit 31 which obtains the device operation information of the user. The device operation information is information indicating how a device was operated, and, for example, is operation history (log information) of the device. The time information (time stamp) indicating the time of the operation is desirably added to the device operation information.

Operation information obtainment device 30 is, for example, an electrical household appliance. Examples of the electrical household appliance include a refrigerator, a cooking appliance (such as an electric pot, a microwave, and a toaster), a vacuum cleaner, a television (TV), and an information device. Examples of obtainment unit 31 include a user interface (for example, a remote control, or, buttons) which receives the operation performed on such an electrical household appliance. When operation information obtainment unit 30 is such an electrical household appliance, operation information obtainment unit 30 transmits, to server device 40, the operation history of the user on obtainment unit 31 as the device operation information.

Although not illustrated in FIG. 1, more specifically, operation information obtainment device 30 includes a timer (timer circuit) for adding time information to the device operation information, a storage which stores the device operation information, and a communication unit which transmits the device operation information to server device 40.

Note that operation information obtainment device 30 may be a device, such as a home energy management system (HEMS) controller, which obtains the history of operation on another device (for example, a control target device) from the another device as operation information.

Moreover, when the details of the operation on a device can be estimated from power consumption, operation information obtainment device 30 may be a device, such as a smart meter or a smart distribution board, which has a power measurement function and a communication function. When operation information obtainment device 30 is a device having the power measurement function and the communication function, operation information obtainment unit 30 transmits information indicating the amount of power consumption as the device operation information. Similarly, operation information obtainment device 30 may be a smart meter which measures the amount of tap water used. Such a smart meter obtains the amount of tap water used as the device operation information for water equipment. In other words, operation information obtainment unit 30 transmits information indicating the amount of tap water used as the device operation information.

The activity amount and the device operation information described above can be used as information for detecting the signs of BPSD. FIG. 2 illustrates information for detecting the signs of behavioral symptoms. FIG. 3 illustrates information for detecting the signs of physiological symptoms.

As illustrated in FIG. 2, among the behavioral symptoms, the signs of wandering can be detected based on the night-time activity amount. The signs of sleep disturbance can be detected based on the activity amount during sleep. The signs of eating disorder can be detected based on the device operation information of, for example, a refrigerator, an electric pot, or a microwave.

As illustrated in FIG. 3, among the psychological symptoms, the signs of depression can be detected based on the daytime activity amount (reduction in activity amount). Moreover, the signs of anxiety can be detected based on the device operation information of TV or an information device (abnormal use of TV or the information device). The signs of misidentification can be detected based on the device operation information of an electrical household appliance (abnormal use of the electrical household appliance).

Next, a configuration of server device 40 will be described. Server device 40 is a device which performs information processing for determining the level of dementia of the user. Server 40 is managed by, for example, a company which operates dementia symptom detection system 10. Server device 40 includes first communication unit 41, information processor 42, and storage 43.

First communication unit 41 receives, from activity amount detection device 20, the activity amount detected by activity amount detection device 20. Moreover, first communication unit 41 receives, from operation information obtainment unit 30, the device operation information obtained by operation information obtainment unit 30. Moreover, first communication unit 41 transmits the presentation information for presenting the level of dementia of the user to second communication unit 51 of information terminal 50 based on the control of information processor 42.

Specifically, first communication unit 41 is a communication module (communication circuit) for wired or wireless communication. Any first communication unit 41 is acceptable which can communicate with activity amount detection device 20, operation information obtainment device 30, and information terminal 50. The communication method (communication standard, communication protocol) of first communication unit 41 is not particularly limited. For example, first communication unit 41 performs communication with activity amount detection device 20, operation information obtainment unit 30, and information terminal 50 through a communication network such as the Internet. Here, devices such as routers may be disposed between first communication unit 41 and each of activity amount detection device 20, operation information obtainment device 30, and information terminal 50.

For example, information processor 42 performs information processing for determining the level of dementia of the user, controls first communication unit 41, and stores information in storage 43. Specifically, information processor 42 identifies (calculates) a reference value for an index corresponding to BPSD, using at least one of the history of the activity amount stored in storage 43 and the history of the device operation information stored in storage 43. Moreover, information processor 42 identifies (calculates) a personal value of the user for the index corresponding to BPSD, using at least one of the detected activity amount of the user and the obtained device operation information of the user. Subsequently, information processor 42 determines the level of dementia of the user based on the identified reference value and the identified personal value. Specifically, information processor 42 is realized by a processor, a microcomputer, or a specialized circuit. The details of a method for calculating the reference value and the personal value will be described later.

Storage 43 is a storage device which stores the activity amount received by first communication unit 41 and the device operation information received by first communication unit 41. Storage 43 stores both (i) the activity amount and the device operation information for calculating the personal value for an index and (ii) the history of the activity amount and the history of the device operation information for calculating a reference value for the index. Specifically, storage 43 is realized by a semiconductor memory, a hard disk drive (HDD) or the like.

Note that the history of the activity amount and the history of the device operation information used for calculating the reference value for the index are, for example, about a user who is the target of the determination of the level of dementia. Accordingly, dementia symptom detection system 10 is capable of detecting the current signs of dementia of the user based on the previous behavior of the user. Moreover, the history of the activity amount and the history of the device operation information used for calculating the reference value for the index may be about another user estimated not to have dementia and different from the user who is the target of the determination of the level of dementia. Accordingly, dementia symptom detection system 10 is capable of detecting the current signs of dementia of the user based on the previous behavior of another user who is normal.

Moreover, storage 43 may store the result of determination of the level of dementia of the user performed by information processor 42, that is, the histories of the personal value and the reference value. Server device 40 is accessible from an external terminal such as information terminal 50.

Therefore, storage of the result of the level of dementia of the user determined by information processor 42 into storage 43 allows the user, the family of the user and the like to refer to the previous determination results by accessing server device 40 by using the external terminal.

Information terminal 50 is a device provided in the user's residence or a device provided in the residence of the family living apart from the user. Moreover, information terminal 50 may be provided in a nursing home. Information terminal 50 may be a device provided in the user's residence, or may be a device carried by, for example, the family living apart from the user, or an employee of the nursing home. Information terminal 50 presents the level of dementia of the user based on the presentation information (display information) output from server device 40.

Specifically, information terminal 50 is, for example, a personal computer, but may be a television, a smart phone, or a tablet terminal. Moreover, information terminal 50 may be a specialized device for use in dementia symptom detection system 10. Information terminal 50 includes second communication unit 51, controller 52, and presentation unit 53.

Second communication unit 51 communicates with first communication unit 41 of server device 40. For example, second communication unit 51 receives presentation information from first communication unit 41. Specifically, second communication unit 51 is a communication module (communication circuit) for wired or wireless communication. Any second communication unit 51 is acceptable which can communicate with first communication unit 41. The communication method (communication standard, communication protocol) of second communication unit 51 is not particularly limited.

Controller 52 causes presentation unit 53 to present the level of dementia of the user, based on the presentation information received by second communication unit 51.

Specifically, controller 52 is realized by a processor, a microcomputer, or a specialized circuit.

Presentation unit 53 presents the level of dementia of the user determined by information processor 42, based on the control of controller 52. Presentation unit 53 displays, for example, an image indicating the level of dementia of the user determined by information processor 42. Specifically, presentation unit 53 is realized by, for example, a liquid crystal panel or an organic electroluminescent (EL) panel.

Operations Performed by Dementia Symptom Detection System

Figure 4:
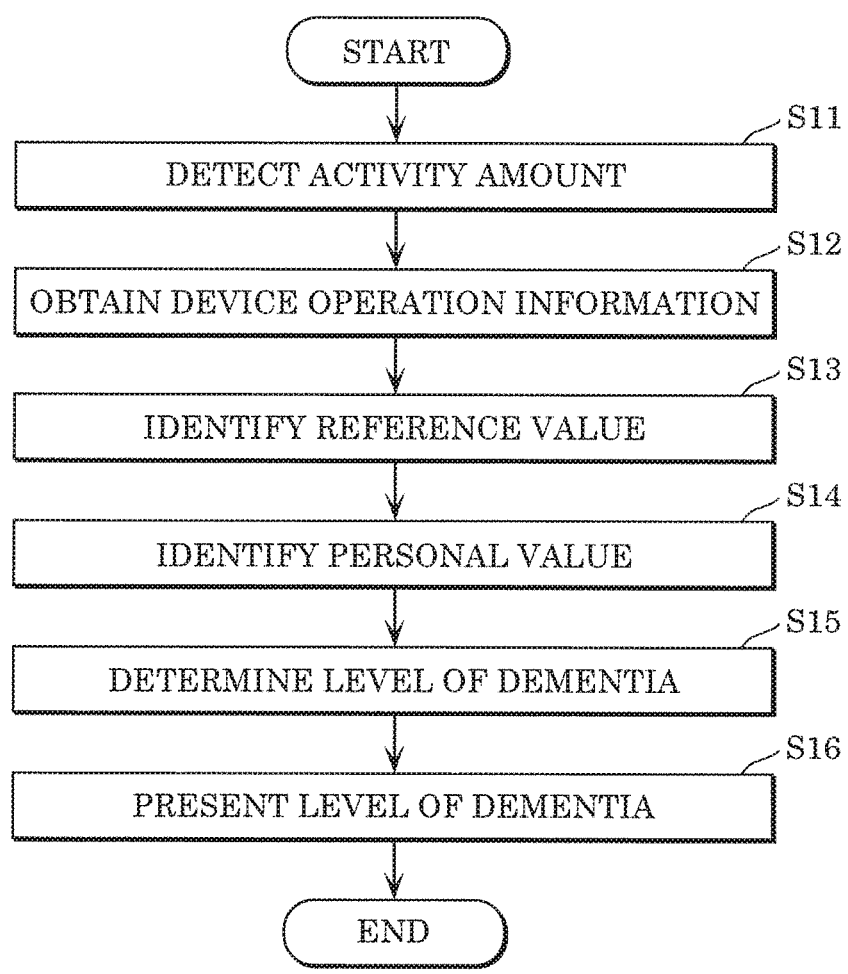
FIG. 4 is a flowchart of the operations performed by the dementia symptom detection system according to the embodiment.

Next, the operations performed by dementia symptom detection system 10 will be described. FIG. 4 is a flowchart of the operations performed by dementia symptom detection system 10. Note that, in the following description of the operations performed by dementia symptom detection system 10, the history of the activity amount and the history of the device operation information are assumed to be stored in storage 43 in advance. For example, the histories of the activity amount and the device operation information for three months are stored.

First, detector 21 of activity detection device 20 detects the activity amount of the user (S11). The detected activity amount of the user is transmitted to first communication unit 41 of server device 40, and is stored in storage 43 by information processor 42. For example, the activity amount of the user for one week is stored.

Similarly, obtainment unit 31 of operation information obtainment unit 30 obtains the device operation information of the user (S12). The obtained device operation information of the user is transmitted to first communication unit 41 of server device 40, and is stored in storage 43 by information processor 42. For example, the device operation information of the user for one week is stored.

Next, information processor 42 identifies a reference value for an index corresponding to BPSD, using at least one of the history of the activity amount stored in storage 43 and the history of the device operation information stored in storage 43 (S13). Moreover, information processor 42 identifies (calculates) a personal value of the user for the index corresponding to the BPSD, using at least one of the activity amount of the user detected by detector 21 in step S11, and the device operation information of the user obtained by obtainment unit 31 in step S12 (S14).

Next, information processor 42 determines the level of dementia of the user based on the reference value identified in step S13 and the personal value of the user identified in step S14 (S15). Information processor 42 generates presentation information (display information) corresponding to the determination result, and causes first communication unit 41 to transmit the generated presentation information. The transmitted presentation information is received by second communication unit 51.

Controller 52 causes presentation unit 53 to present the level of dementia of the user based on the presentation information. In other words, presentation unit 53 presents the level of dementia of the user determined by information processor 42, based on the control of controller 52 (S16).

Specific Example 1 of Method for Identifying Reference Value and Personal Value

Next, a specific example of a method for identifying a reference value and a personal value will be described. In the following description, a description will be given of a method for calculating a reference value and a personal value for each of three indices of action amount, memory loss, and executive ability as indices corresponding to the BPSD. These three indices are one example. The indices used in the information processing performed by information processor 42 are only required to be determined so as to correspond to the BPSD. The types of the indices are not particularly limited.

Figure 5:
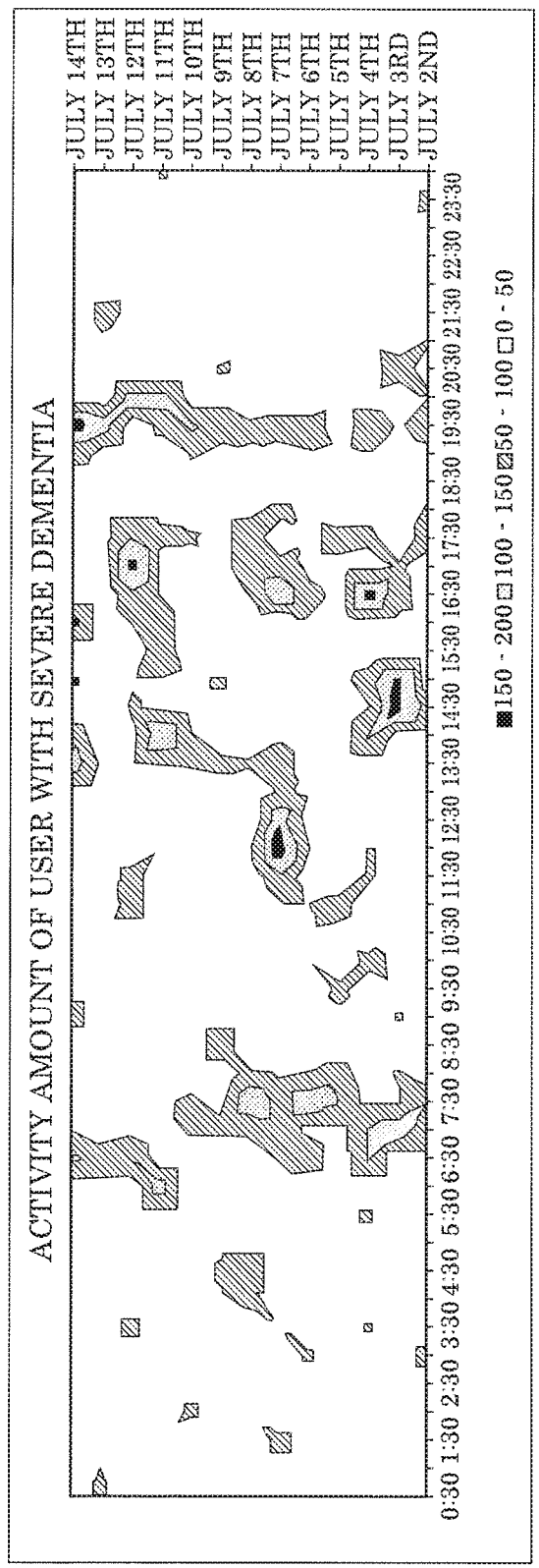
FIG. 5 illustrates mapped data of the activity amount of a user with severe dementia.
Figure 6:
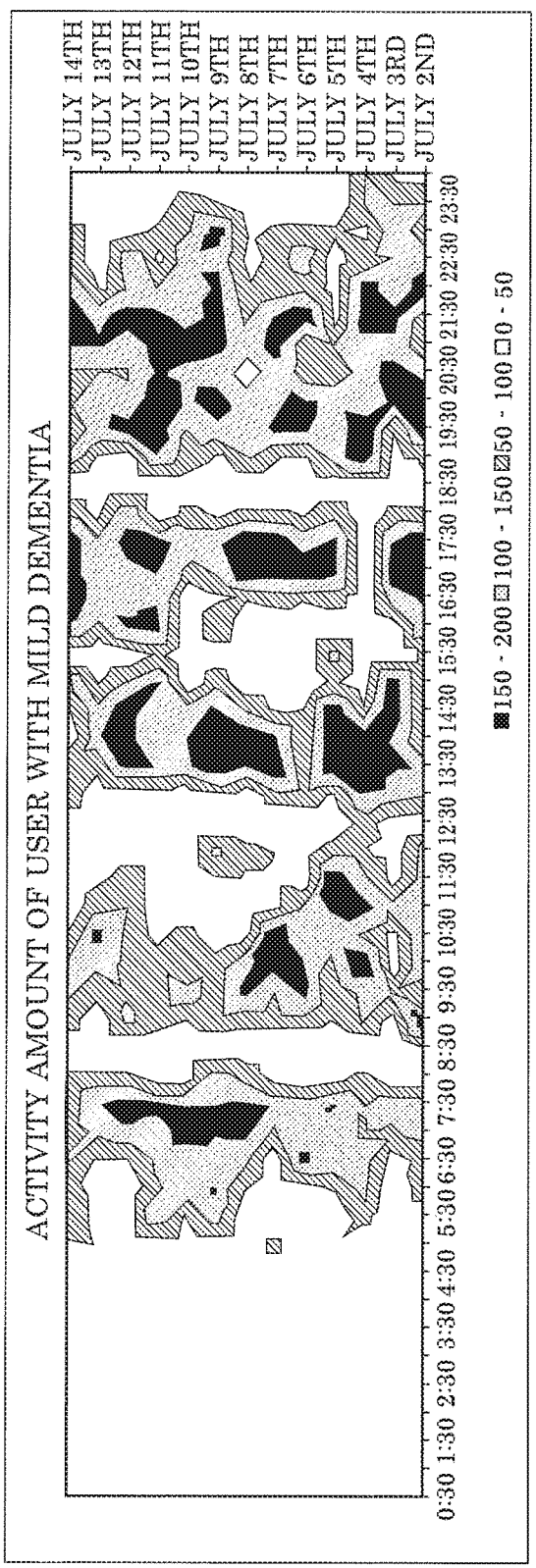
FIG. 6 illustrates mapped data of the activity amount of a user with mild dementia.
Figure 7:
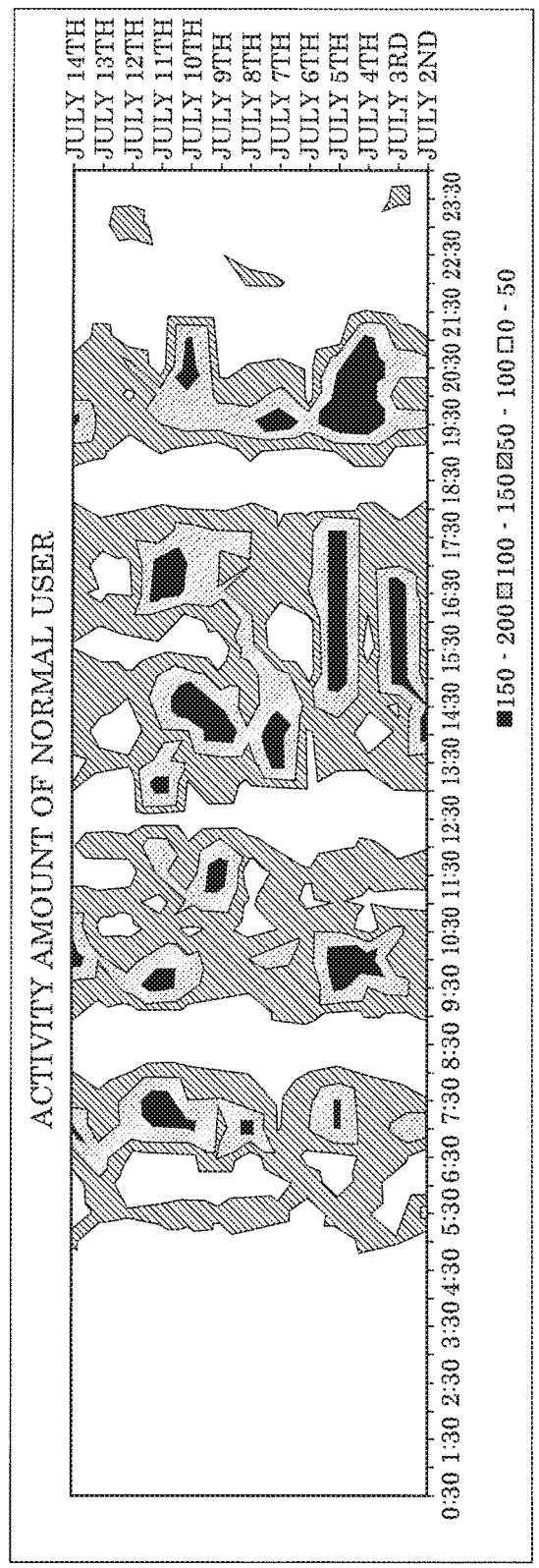
FIG. 7 illustrates mapped data of the activity amount of a normal user.

First, a description will be given of a method for calculating a reference value and a personal value for the index of action amount. It may be considered that the index of action amount is approximately equal to the activity amount. FIG. 5 illustrates mapped data of the activity amount of a user with severe dementia. FIG. 6 illustrates mapped data of the activity amount of a user with mild dementia. FIG. 7 illustrates mapped data of the activity amount of a normal user. In each of FIG. 5 to FIG. 7, the vertical axis represents date, the horizontal axis represents time, and a darker portion indicates a higher activity amount. In each of FIG. 5 to FIG. 7, the activity amount is quantified at 0 to 200 inclusive, and is color coded in four levels, but the activity amount may be color coded in five or more levels.

As illustrated in FIG. 5 to FIG. 7, the daytime activity amount (for example, from 8:00 to 18:00) of a user with the signs of dementia tends to be low. Therefore, information processor 42 calculates the daily average value of the daytime activity amount of the user as a personal value for the action amount. Moreover, information processor 42 calculates the daily average value of the daytime activity amount using the history of the activity amount, and determines the calculated average value as the reference value.

Information processor 42 determines that the user has no signs of dementia, for example, when the personal value for the index of action amount is greater than or equal to the reference value. In contrast, information processor 42 determines that the user has signs of dementia, for example, when the personal value for the index of action amount is less than the reference value. Here, information processor 42 determines that caution regarding dementia needs to be expressed to the user, when the difference between the personal value and the reference value is less than a threshold value. Moreover, information processor 42 determines that warning regarding dementia needs to be expressed to the user, when the difference between the personal value and the reference value is greater than or equal to the threshold value.

Note that the above method is an example of the method for determining the level of dementia. The method for determining the threshold value and the like is not particularly limited. For example, the determination may be made according to, for example, the percentage of the personal value relative to the reference value.

Moreover, as illustrated in FIG. 5 to FIG. 7, sleep of a user with the signs of dementia becomes non-periodic due to wandering and the like, and thus, the night-time activity amount (for example, from 21:00 to 5:00 of the following morning) tends to greatly vary from day to day. Therefore, information processor 42 calculates the variations (the variation amount) in night-time activity amount of the user as the personal value for the action amount. Moreover, information processor 42 calculates the variations in night-time activity amount using the history of the activity amount, and determines the calculated average value as a reference value.

Information processor 42 determines that the user has no signs of dementia, for example, when the personal value for the index of action amount is less than or equal to the reference value. In contrast, information processor 42 determines that the user has signs of dementia, for example, when the personal value for the index of action amount is greater than the reference value. Here, information processor 42 determines that caution regarding dementia needs to be expressed to the user, when the difference between the personal value and the reference value is less than a threshold value. Moreover, information processor 42 determines that warning regarding dementia needs to be expressed to the user, when the difference between the personal value and the reference value is greater than or equal to the threshold value.

Specific Example 2 of Method for Identifying Reference Value and Personal Value

Figure 8:
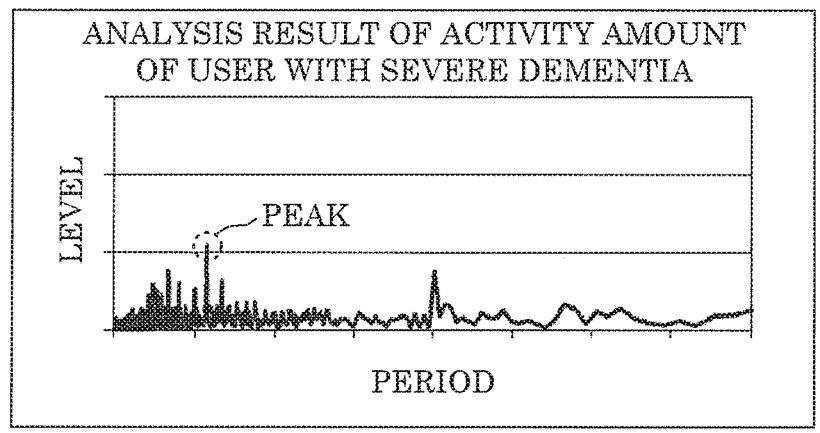
FIG. 8 illustrates a frequency analysis result of the daily activity amount of a user with severe dementia.
Figure 9:
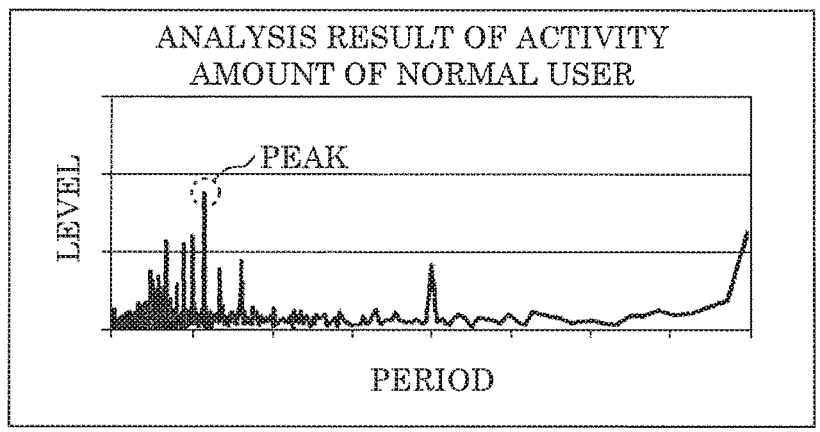
FIG. 9 illustrates a frequency analysis result of the daily activity amount of a normal user.

As illustrated in FIG. 5 to FIG. 7, a user with the signs of dementia tends to have irregular habits, and thus, the periodicity of the activity amount is low. Moreover, the user with the signs of dementia has less instrumental activities of daily living which require complicated and many actions, and thus the amount of short-period activity is reduced. Therefore, the reference value and the personal value each may be a value which indicates the periodicity of the action amount (activity amount). Specifically, information processor 42 may perform frequency analysis, such as discrete Fourier transform (DFT) on a signal indicating the temporal change in activity amount, to identify a value which indicates the periodicity. FIG. 8 illustrates a frequency analysis result of the daily activity amount of a user with severe dementia. FIG. 9 illustrates a frequency analysis result of the daily activity amount of a normal user. In each of FIG. 8 and FIG. 9, the horizontal axis represents period (1/frequency).

In many cases, the period of instrumental activities of daily living is generally four hours or less. In such a period of the instrumental activities of daily living, as illustrated in FIG. 8 and FIG. 9, the peak level obtained through the frequency analysis on the activity amount of a user with severe dementia is lower than the peak level obtained through the frequency analysis on the activity amount of a normal user. Information processor 42 may determine such a peak level as the reference value and the personal value. The peak level is an example of a value indicating the periodicity of the action amount (activity amount).

Information processor 42 determines that the user has no signs of dementia, when the peak level based on the activity amount of the user is higher than the peak level determined as a reference value. Moreover, information processor 42 determines that the user has signs of dementia, when the peak level based on the activity amount of the user is lower than or equal to the peak level determined as the reference value. Here, information processor 42 determines that caution regarding dementia needs to be expressed to the user, when the difference between the peak level of the user and the peak level determined as the reference value is less than a threshold value. Moreover, information processor 42 determines that warning regarding dementia needs to be expressed to the user, when the difference between the peak level of the user and the peak level determined as the reference value is greater than or equal to the threshold value.

Note that the value which indicates the periodicity of the action amount is not limited to the peak level. For example, the half width of the peak may be used as a value which indicates the action amount. In this case, information processor 42 determines that the level of dementia is milder as the half width of the peak increases. It is because the periodicity is considered to be lower as the half width of the peak increases.

Moreover, the periodicity of the action amount of the user may be calculated based on information which indicates the amount of power consumption (hereinafter, may also be referred to as power consumption data) which is an example of the device operation information. It is because when the user periodically performs activity, electric power is periodically used according to the activity.

The power consumption data of a normal user tends to have the same levels of power consumption amount at specific times. In other words, it can be said that the power consumption data of a normal user has higher periodicity. In contrast, the power consumption data of a user with signs of dementia has lower periodicity.

Figure 10:
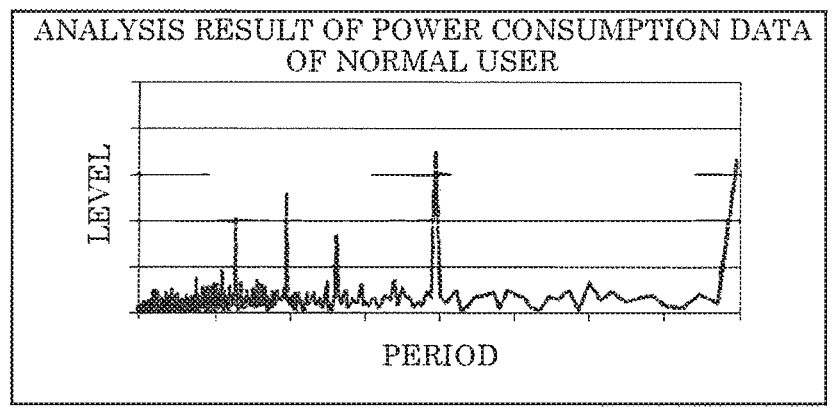
FIG. 10 illustrates a frequency analysis result of the daily power consumption data of the normal user.
Figure 11:
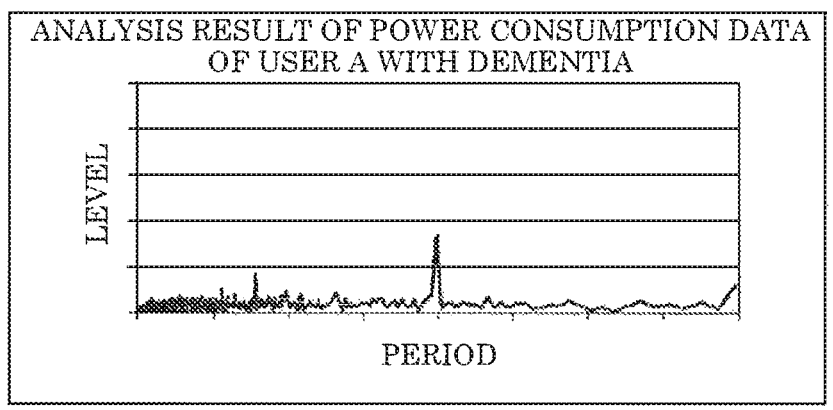
FIG. 11 illustrates a frequency analysis result of the daily power consumption data of user A with the signs of dementia.
Figure 12:
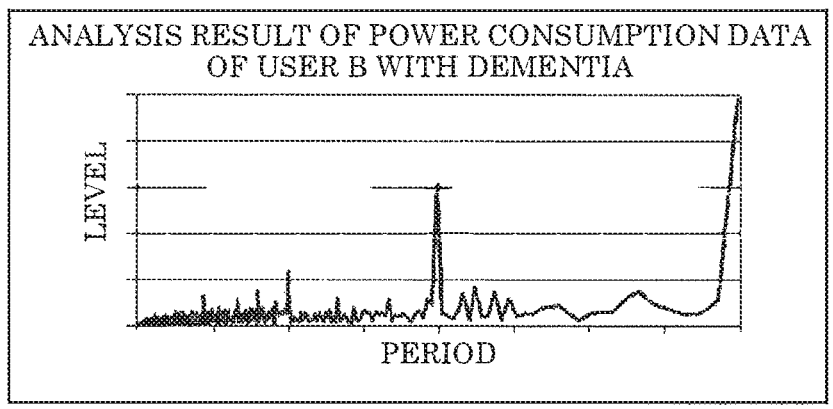
FIG. 12 illustrates a frequency analysis result of the daily power consumption data of user B with the signs of dementia.

In this manner, the power consumption data and the signs of dementia are considered to be correlated to each other. Accordingly, information processor 42 is capable of obtaining a value which indicates the periodicity of the action amount (activity amount) by performing frequency analysis on such power consumption data. FIG. 10 illustrates a frequency analysis result of daily power consumption data of a normal user. FIG. 11 illustrates a frequency analysis result of daily power consumption data of user A with the signs of dementia. FIG. 12 illustrates a frequency analysis result of daily power consumption data of user B with the signs of dementia. In each of FIG. 10 to FIG. 12, the horizontal axis represents period (1/frequency).

As illustrated in FIG. 10 to FIG. 12, the peak level obtained through the frequency analysis on the power consumption data of a user with the signs of dementia is lower than the peak level obtained through the frequency analysis on the power consumption data of a normal user. Therefore, information processor 42 may determine such a peak level as the reference value and the personal value. The method for determining the dementia symptoms using the peak level is as described above. Moreover, instead of the peak level, the half width of the peak may be used as a value indicating the periodicity of the action amount.

Moreover, as illustrated in FIG. 10 to FIG. 12, the number of peaks obtained through the frequency analysis on the power consumption data of a user with the signs of dementia is less than the number of peaks obtained through the frequency analysis on the power consumption data of a normal user. Therefore, information processor 42 may determine the number of peaks exceeding a predetermined level as a reference value and a personal value. In this case, the number of peaks is an example of a value indicating the periodicity of the action amount (activity amount).

Information processor 42 determines that the user has no signs of dementia, when the number of peaks based on the power consumption data of the user is greater than the number of peaks determined as a reference value. Moreover, information processor 42 determines that the user has signs of dementia, when the number of peaks based on the power consumption data of the user is less than or equal to the number of peaks determined as the reference value. Here, information processor 42 determines that caution regarding dementia needs to be expressed to the user, when the difference between the number of peaks of the user and the number of peaks determined as the reference value is less than a threshold value. Moreover, information processor 42 determines that warning regarding dementia needs to be expressed to the user, when the difference between the number of peaks of the user and the number of peaks determined as the reference value is greater than or equal to the threshold value. Note that the method for determining the symptoms of dementia based on the number of peaks may be combined with the determination method based on the activity amount descried above.

As described above, information processor 42 may determine that the level of dementia of the user is milder when the personal value indicates periodicity higher than the periodicity indicated by the reference value than when the personal value indicates periodicity lower than the periodicity indicated by the reference value.

Specific Example 3 of Method for Identifying Reference Value and Personal Value

Next, a description will be given of a method for calculating a reference value and a personal value for the index of memory loss. For example, when tap water is continuously used for a predetermined period or longer, it is considered that the user has forgotten to turn off the faucet. Therefore, when operation information obtainment unit 30 transmits the amount of tap water used as the device operation information, information processor 42 is capable of quantifying the index of memory loss based on the number of times that use of tap water continues for a predetermined period or longer. Moreover, when the time during which a refrigerator door is left open continues for a predetermined period or longer, it is considered that the user has forgotten to close the refrigerator door. Therefore, when the time during which the refrigerator door is left open can be identified based on the device operation information, information processor 42 is capable of quantifying the index of memory loss based on the number of times that the time during which the refrigerator door is left open continues for a predetermined period or longer.

Information processor 42 identifies a personal value based on the device operation information of the user, and identifies a reference value based on the history of the device operation information stored in storage 43. For example, when it is quantified in such a manner that a smaller value indicates more severe memory loss (more severe signs of dementia), information processor 42 determines that the user has no signs of dementia, when, for example, the personal value for the index of memory loss is greater than or equal to a reference value. In contrast, information processor 42 determines that the user has signs of dementia, when, for example, the personal value for the index of memory loss is less than the reference value. Here, information processor 42 determines that caution regarding dementia needs to be expressed to the user, when the difference between the personal value and the reference value is less than a threshold value. Moreover, information processor 42 determines that warning regarding dementia needs to be expressed to the user, when the difference between the personal value and the reference value is greater than or equal to the threshold value.

Note that when identifying the value for the index of memory loss, only the device operation information is typically used, but the activity amount may also be used together. This allows information processor 42 to have increased accuracy in value for the index of memory loss.

For example, when activity amount detection device 20 is provided in each room of the residence and operation information obtainment device 30 transmits the amount of power consumption as the device operation information, and when the amount of power consumption is large in a room where the activity amount is 0 (or extremely low) for a predetermined period or longer, it is suspected that electrical equipment such as lighting equipment is left on. Accordingly, information processor 42 may quantify the index of memory loss based on, for example, the number of times such a situation occurred.

Specific Example 4 of Method for Identifying Reference Value and Personal Value

Next, a description will be given of a method for calculating a reference value and a personal value for index of executive ability. When the signs of dementia of the user becomes severe, the user tends to move slower and executive ability tends to be reduced. Reduction in executive ability causes such signs as longer hours of use of a cooking appliance.

Accordingly, the index of executive ability is identified based on, for example, the device operation information of a cooking appliance. Specifically, information processor 42 identifies the index of executive ability according to hours of use of the cooking appliance indicated by the device operation information. For example, when it is determined that a smaller value indicates a more severe sign of dementia, information processor 42 quantifies the personal value and the reference value in such a manner that the index of executive ability decreases as the hours of use of the cooking appliance indicated by the device operation information increases Information processor 42 determines that the user has no signs of dementia, when the personal value for the index of executive ability is greater than or equal to the reference value. In contrast, information processor 42 determines that the user has signs of dementia, when the personal value for the index of executive ability is less than the reference value. Here, information processor 42 determines that caution regarding dementia needs to be expressed to the user, when the difference between the personal value and the reference value is less than a threshold value. Moreover, information processor 42 determines that warning regarding dementia needs to be expressed to the user, when the difference between the personal value and the reference value is greater than or equal to the threshold value.

When a user with reduced executive ability operates a remote control of TV, channel surfing (forward operation and backward operation) increases compared to directly designating a channel. Accordingly, when obtainment unit 31 is a remote control of TV, information processor 42 may quantify the index of executive ability based on the frequency at which the channel surfing is performed.

Example of Image to be Presented

Figure 13:
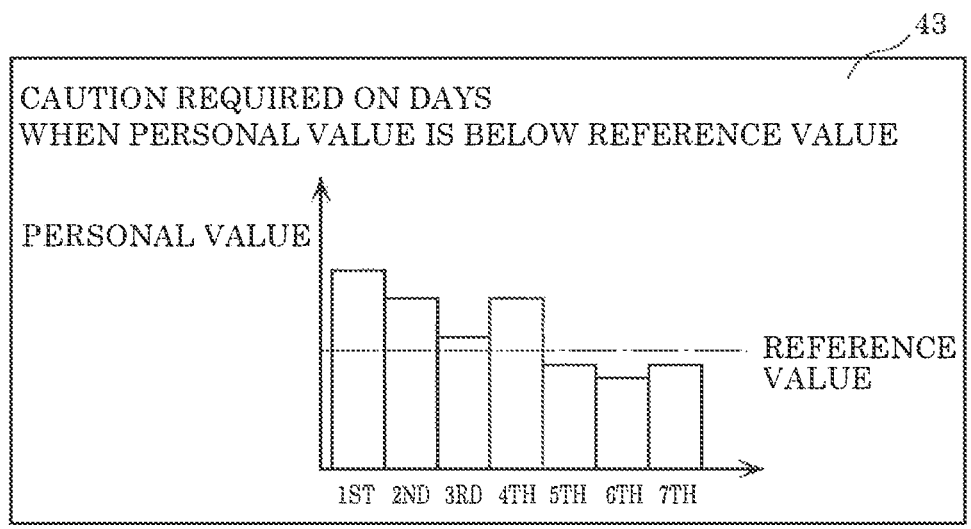
FIG. 13 illustrates an example of an image which shows changes in daily personal value for one index.

Next, an example of an image to be presented by presentation unit 53 will be described. As described above, information processor 42 identifies, for example, a personal value and a reference value for one index, and compares the identified personal value with the identified reference value to determine the level of dementia. For example, when a personal value is identified daily, as illustrated in FIG. 13, changes in daily personal value for one index may be presented. FIG. 13 illustrates an example of an image which shows changes in daily personal value for one index. In FIG. 13, a reference value is also shown.

Figure 14:
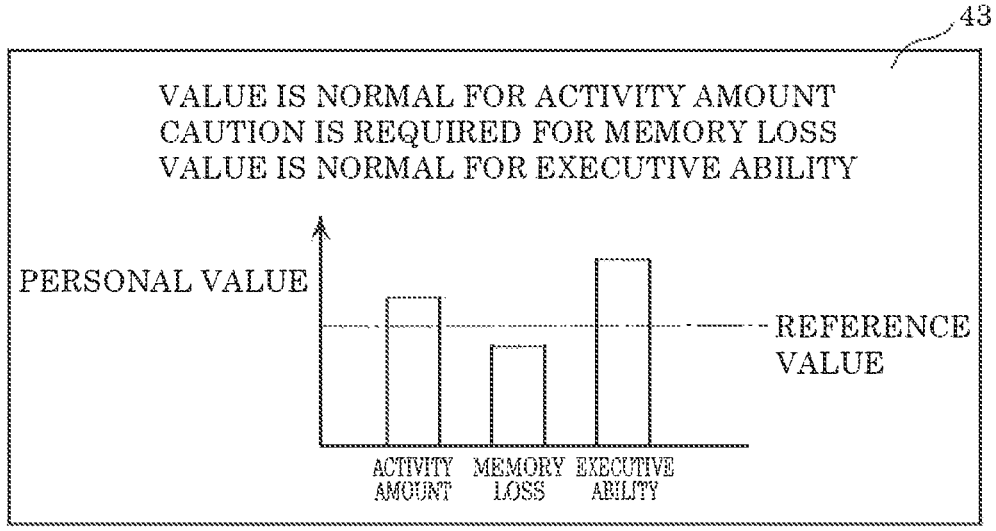
FIG. 14 illustrates an example of an image which separately shows personal values for three indices.

Moreover, it may be that information processor 42 identifies a personal value and a reference value for each of three indices, and an image to be presented by information presentation unit 53 may separately show the identified personal values for three indices. FIG. 14 illustrates an example of an image which separately shows personal values for three indices. In the image in FIG. 14, bar graphs corresponding to the three indices are shown, and a reference value is also shown.

Note that information processor 42 may comprehensively determine the level of dementia of the user using a plurality of indices. For example, information processor 42 may determine the level of dementia of the user by comparing the total of three personal values corresponding to three indices and the total of three reference values corresponding to the three indices. Moreover, for example, information processor 42 may determine the level of dementia of the user based on the number of indices for which the personal value indicates a level of dementia more severe than the level of dementia indicated by the reference value among a plurality of indices.

Moreover, as illustrated in the graphs of FIG. 13, information processor 42 may determine that the user has signs of dementia, when a state where the personal value indicates a level of dementia more severe than the level of dementia indicated by the reference value continues for a predetermined period or longer, such as the state where the personal value is below the reference value for at least predetermined days.

Moreover, in the above embodiment, the levels of dementia are classified into three levels which are normal, caution, and warning, but the levels of dementia may be classified into at least two levels.

Moreover, the display mode may differ for each level of dementia as described above. For example, it may be that the graph indicating a normal level is displayed in blue, the graph indicating caution is displayed in yellow, and the graph indicating warning is displayed in red.

The level of dementia does not need to be indicated by using graphs, but may be indicated by using values. In this case, for example, the font of the values (such as color or the size of letters) may differ for each level of dementia.

Another Method for Determining Level of Dementia

Figure 15:
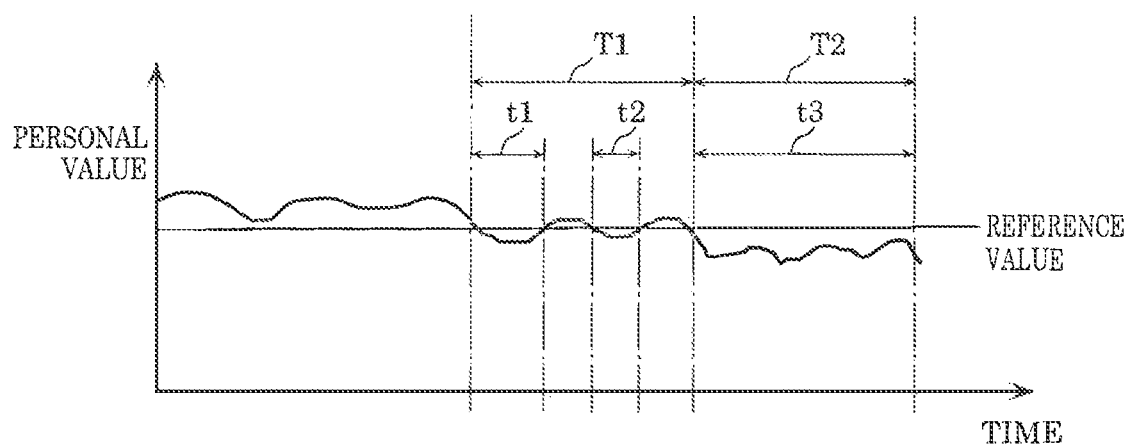
FIG. 15 illustrates an example of another method for determining the level of dementia.

Next, another method for determining the level of dementia will be described. FIG. 15 illustrates an example of another method for determining the level of dementia. Note that, in the following description, it is assumed that the greater the personal value is, the more normal the level is (no signs of dementia).

For example, when data of the identified daily personal values for one month is available, as illustrated in FIG. 15, the temporal change in personal value for one month can be obtained.

Here, information processor 42 compares the reference value and the personal values to identify a first period during which the personal value indicates a severe level of dementia. Specifically, the first period is, for example, a period during which the personal value is below the reference value. In FIG. 15, the first period is period t1, period t2, and period t3.

Next, information processor 42 determines the level of dementia of the user during predetermined second period T1, based on the length of the first period included in second period T1. The length of the first period included in second period T1 is the total of period t1 and period t2. Specifically, information processor 42 determines that as the length of the first period increases, the level of dementia is more severe. During predetermined second period T2 which is equal in length to predetermined second period T1, the personal value is below the reference value in the entire period (period t3). Accordingly, information processor 42 is capable of determining that the user has more signs of dementia in second period T2 compared to in second period T1.

In this way, determination of the level of dementia based on the temporal change in personal value leads to accurate determination of the level of dementia.

Figure 16:
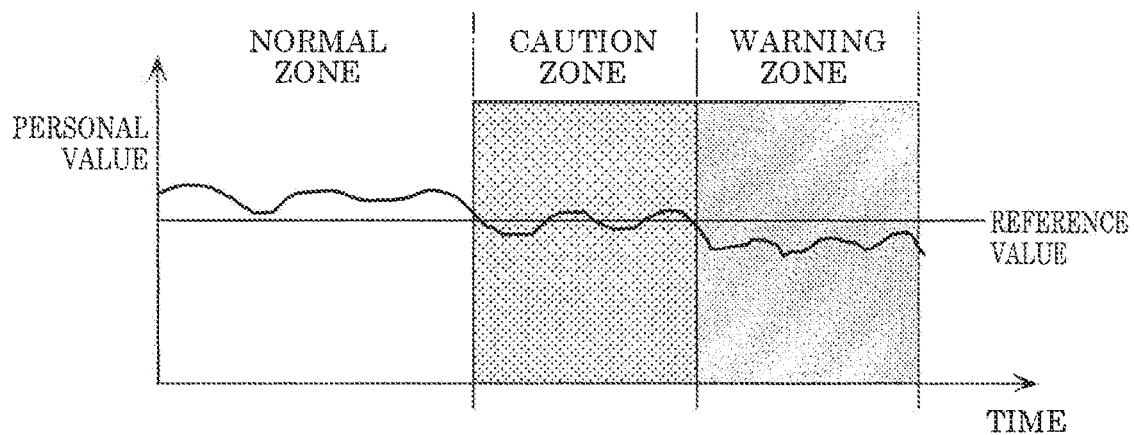
FIG. 16 illustrates another example of an image to be presented by a presentation unit.

Note that, in the another determining method as described above, presentation unit 53 may present the graph indicating the temporal change as illustrated in FIG. 15. Here, presentation unit 53 may present the level of dementia of the user in different modes according to the level. FIG. 16 illustrates another example of an image to be presented by presentation unit 53.

In the example of FIG. 16, the colors of the background of the graph differ according to the level of dementia. For example, a normal zone is a zone where the personal value is greater than the reference value and no signs of dementia is found. Accordingly, the background of the normal zone is displayed in white In contrast, the caution zone is a zone where the user has a slight sign of dementia. Accordingly, the background of the caution zone is displayed in yellow. The warning zone is a zone where the user has signs of dementia.

Accordingly, the background of the warning zone is displayed in red.

Figure 17:
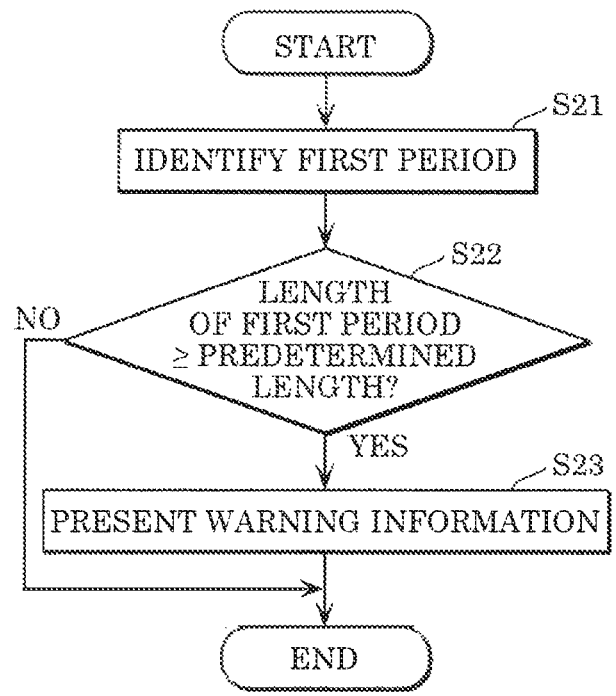
FIG. 17 is a flowchart of the operations performed when warning information is presented.

When the signs of dementia are severe as in the warning zone, warning information (warning image) for expressing warning to the user or the family of the user may be presented. Specifically, when the signs of dementia are severe refers to when the length of the first period included in the predetermined second period is greater than or equal to a predetermined length. Note that the predetermined length is, for example, 60% of the length of the second period, but the present invention is not limited to the example. FIG. 17 is a flowchart of the operations performed when warning information is presented.

Figure 18:
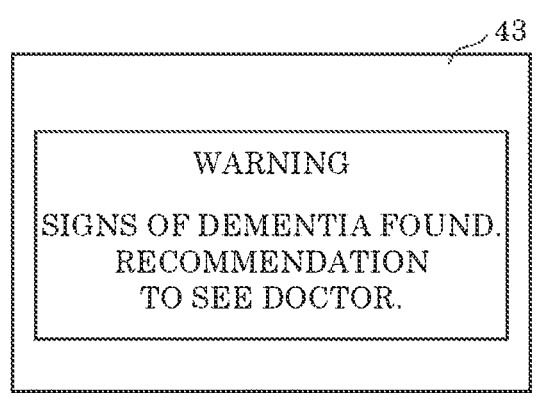
FIG. 18 illustrates an example of the warning information.

First, information processor 42 identifies a first period during which the personal value indicates a level of dementia more severe than the level of dementia indicated by the reference value (S21). Subsequently, information processor 42 determines whether the length of the first period included in a predetermined second period is greater than or equal to a predetermined length (S22). When information processor 42 determines that the length of the first period included in the predetermined second period is greater than or equal to the predetermined length (Yes in S22), presentation unit 53 presents warning information (S23). FIG. 18 illustrates an example of the warning information. In the example illustrated in FIG. 18, the warning information includes a message which recommends seeing a doctor. Such warning information can express, to the user or the family of the user, warning that the signs of dementia are severe.

In contrast, when information processor 42 determines that the length of the first period included in the predetermined second period is less than the predetermined length (No in S22), the operations end.

Advantageous Effects, Etc.

As described above, dementia symptom detection system 10 includes: detector 21 which detects the activity amount of a user; obtainment unit 31 which obtains device operation information of the user; and storage 43 which stores the history of the activity amount and the history of the device operation information. Moreover, dementia symptom detection system 10 includes information processor 42 which determines the level of dementia of the user based on (i) a reference value which is for an index corresponding to BPSD and which is determined based on at least one of the history of the activity amount stored in storage 43 and the history of the device operation information stored in storage 43 and (ii) a personal value of the user which is for the index and which is determined based on at least one of the detected activity amount of the user and the obtained device operation information of the user. Dementia symptom detection system 10 includes presentation unit 53 which presents the level of dementia of the user determined by information processor 42.

In this way, the index corresponding to the BPSD is used for determining the level of dementia, which allows dementia symptom detection system 10 to appropriately detect the signs of dementia. Moreover, dementia symptom detection system 10 is capable of presenting the presence of the signs of dementia, which allows early recognition of dementia symptoms.

Moreover, it may be that information processor 42 identifies a first period during which the personal value indicates a level of dementia more severe than the level of dementia indicated by the reference value, to determine the level of dementia of the user during a predetermined second period based on the length of the first period included in the predetermined second period. Moreover, presentation unit 53 may present the level of dementia of the user in different modes according to the level.

In this way, the level of dementia is determined based on the temporal change in personal value, which allows dementia symptom detection system 10 to accurately determine the level of dementia.

Moreover, presentation unit 53 may present warning information when the length of the first period included in the second period is greater than or equal to a predetermined length.

With this, dementia symptom detection system 10 is capable of expressing, to the user or the family of the user, warning that the signs of dementia are severe.

Moreover, it may be that the index indicates the action amount, and that each of the reference value and the personal value is a value indicating periodicity of the action amount. Information processor 42 may determine that the level of dementia of the user is milder when the personal value indicates periodicity higher than the periodicity indicated by the reference value than when the personal value indicates periodicity lower than the periodicity indicated by the reference value.

With this, dementia symptom detection system 10 is capable of determining the level of dementia of the user based on the periodicity of the action amount.

Moreover, it may be that storage 43 stores the determination result of the level of dementia of the user, and that dementia symptom detection system 10 further includes server device 40 including storage 43.

In this way, the previous determination results are stored into storage 43 included in server device 40, which allows dementia symptom detection system 10 to present the previous determination results.

Moreover, server device 40 may be accessible from an external terminal.

With this, the user, the family of the user, and the like are capable of referring to the previous determination results by accessing server device 40 by using the external terminal.

Moreover, it may be that storage 43 stores the history of the activity amount of the user and the history of the device operation information of the user, and that the reference value is determined based on the history of the activity amount of the user stored in storage 43 and the history of the device operation information of the user stored in storage 43.

With this, dementia symptom detection system 10 is capable of detecting the current signs of dementia of the user based on the previous behavior of the user.

Moreover, it may be that storage 43 stores the histories of the activity amount and device operation information of another user who is different from the user and estimated not to have dementia. It may be that the reference value is determined based on the history of the activity amount of the another user stored in storage 43 and the history of the device operation information of the another user stored in storage 43.

With this, dementia symptom detection system 10 is capable of detecting the current signs of dementia of the user based on the previous behavior of another user who is normal.

Other Embodiments

The dementia symptom detection system according to the above embodiment has been described, but the present invention is not limited to the embodiment.

For example, the way the structural elements included in the dementia symptom detection system are assigned to the respective devices described above is an example. Each structural element included in the dementia symptom detection system may be assigned in any way as long as the level of dementia of the user can be determined. For example, the storage included in the server device may be realized as a separate storage device.

Moreover, the processing performed by the information processor included in the server device in the above embodiment may be performed by a controller included in the information terminal. In other words, the information terminal may determine the level of dementia. In this case, the information terminal receives the activity amount from the activity amount detection device (detector), and receives the device operation information from the operation information obtainment device (obtainment unit).

Moreover, each of the structural elements in the above-described embodiment may be configured in the form of an exclusive hardware product, or may be realized by executing a software program suitable for the structural element. Each of the structural elements may be realized by means of a program executing unit, such as a central processing unit (CPU) or a processor, reading and executing the software program recorded on a recording medium such as a hard disk or a semiconductor memory.

Moreover, each of the structural elements may be a circuit (or integrated circuit). These circuits may be configured as a single circuit, or may be individual circuits. Moreover, these circuits may be ordinary circuits, or may be specialized circuits.

Moreover, general or specific aspects of the present invention may be realized using, for example, a system, a device, a method, an integrated circuit, a computer program, or a computer-readable recording medium such as a CD-ROM. Alternatively, the general or specific aspects of the present invention may be realized using any combination of systems, devices, methods, integrated circuits, computer programs, or computer-readable recording media. For example, an aspect of the present invention may be realized as a dementia symptom detection device which performs the processing executed by the information processor in the above embodiment, or may be realized as a program for causing a computer to function as the dementia symptom detection system or the dementia symptom detection device. Moreover, an aspect of the present invention may be realized as a method for determining the level of dementia (information presentation method) executed by the dementia symptom detection system or the dementia symptom detection device.

Moreover, the order of processing in the operations of the dementia symptom detection system described in the above embodiment is an example. The order of the processing may be changed or executed in parallel. Moreover, the processing executed by a specific processor may be executed by another processor.

The scope of the present invention may also include embodiments as a result of adding various modifications to the embodiments that may be conceived by those skilled in the art, and embodiments obtained by combining structural elements and functions in the embodiments in any manner as long as the combination does not depart from the spirit of the present invention.

The invention claimed is:

1. A dementia symptom detection system comprising:
   an electronic sensor which detects an activity amount of a user;
   a user interface which obtains device operation information of the user;
   a memory which stores a history of the activity amount and a history of the device operation information;
   an information processor which determines a level of dementia of the user based on (i) a reference value for an index corresponding to behavioral and psychological symptoms of dementia, and (ii) a personal value of the user for the index,
      wherein the reference value is determined based on at least one of the history of the activity amount stored in the memory and the history of the device operation information stored in the memory;
      wherein the personal value is determined based on at least one of the activity amount of the user detected and the device operation information of the user obtained;
      wherein the index indicates an action amount and each of the reference value and the personal value is a value indicating periodicity of the action amount;
      wherein the information processor determines that the level of dementia of the user is milder when the personal value indicates periodicity higher than periodicity indicated by the reference value; and
      wherein the information processor determines that the level of dementia of the user is more severe when the personal value indicates periodicity lower than periodicity indicated by the reference value; and
   a display which presents the level of dementia of the user determined by the information processor in different display modes according to the level of dementia of the user,
      wherein the display presents the level of dementia of the user in a first display mode when the information processor determines that the level of dementia of the user is milder, and
      wherein the display presents the level of dementia of the user in a second display mode when the information processor determines that the level of dementia of the user is more severe, the second display mode including warning information recommending the user to seek medical attention.

2. The dementia symptom detection system according to claim 1,
   wherein the information processor identifies a first period during which the personal value indicates a personal value level of dementia more severe than a reference value level of dementia indicated by the reference value, and determines the level of dementia of the user during a predetermined second period based on a length of the first period included in the predetermined second period.

3. The dementia symptom detection system according to claim 2,
   wherein the display presents warning information when the length of the first period included in the predetermined second period is greater than or equal to a predetermined length.

4. The dementia symptom detection system according to claim 1,
   wherein the memory stores a determination result of the level of dementia of the user, and
   the dementia symptom detection system further comprises a server device including the memory.

5. The dementia symptom detection system according to claim 4,
   wherein the server device is accessible from an external terminal.

6. The dementia symptom detection system according to claim 1,
   wherein the memory stores the history of the activity amount of the user and the history of the device operation information of the user, and
   the reference value is determined based on the history of the activity amount of the user stored in the memory and the history of the device operation information of the user stored in the memory.

7. The dementia symptom detection system according to claim 1,
   wherein the memory stores a history of an activity amount of another user and a history of device operation information of the another user, the another user being different from the user and estimated not to have dementia, and
   the reference value is determined based on the history of the activity amount of the another user stored in the memory and the history of the device operation information of the another user stored in the memory.

8. The dementia symptom detection system according to claim 1, wherein the electronic sensor is at least one selected from a pyroelectric sensor, an infrared sensor, a Doppler sensor, a radio wave sensor, and an acceleration sensor.

9. The dementia symptom detection system according to claim 1, wherein the user interface is at least one selected from a remote control and buttons.

10. The dementia symptom detection system according to claim 1, wherein the memory is at least one selected from a semiconductor memory and a hard disk drive.

11. The dementia symptom detection system according to claim 1, wherein the display is at least one selected from a liquid crystal panel and an organic electroluminescent panel.

12. A non-transitory computer-readable recording medium for use in a computer, the recording medium having a computer program recorded thereon for causing the computer to function as the dementia symptom detection system according to claim 1.

* * * * *